United States Patent
Kamezaki (10) Patent No.: US 10,145,752 B2
(45) Date of Patent: Dec. 4, 2018

(54) MANAGEMENT APPARATUS FOR MEASUREMENT EQUIPMENT

(71) Applicant: HORIBA, LTD., Kyoto (JP)

(72) Inventor: Ritsuko Kamezaki, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/409,673

(22) Filed: Jan. 19, 2017

(65) Prior Publication Data

US 2017/0212001 A1 Jul. 27, 2017

(30) Foreign Application Priority Data

Jan. 21, 2016 (JP) ................................ 2016-010190

(51) Int. Cl.
- *G01L 23/08* (2006.01)
- *G01L 19/08* (2006.01)
- *G16H 40/40* (2018.01)

(52) U.S. Cl.
CPC ............ *G01L 23/08* (2013.01); *G01L 19/083* (2013.01); *G16H 40/40* (2018.01)

(58) Field of Classification Search
CPC ... G01L 19/083; G01L 23/08; G06F 19/3412; G06F 17/30575; G06F 19/00; G06Q 10/06; H04L 63/10
USPC ........................ 702/19, 33, 35, 59, 122, 125
See application file for complete search history.

(56) References Cited

U.S. PATENT DOCUMENTS

| | | | | |
|---|---|---|---|---|
| 2002/0054141 | A1* | 5/2002 | Yen | G06F 3/0481 715/804 |
| 2006/0271758 | A1* | 11/2006 | Innan | G06F 3/0605 711/170 |
| 2008/0262776 | A1 | 10/2008 | Yamasaki et al. | |
| 2011/0077536 | A1 | 3/2011 | Kubo | |
| 2015/0278325 | A1* | 10/2015 | Masuda | G06F 17/30575 707/624 |
| 2016/0005296 | A1* | 1/2016 | Kil | G08B 21/20 340/604 |
| 2016/0284109 | A1* | 9/2016 | Nishimura | G06T 11/206 |

FOREIGN PATENT DOCUMENTS

JP   2008-249590   10/2008

OTHER PUBLICATIONS

Extended European Search Report for European Application No. 17152356.6-1952 dated May 9, 2017.

* cited by examiner

*Primary Examiner* — Shahed Ahmed
(74) *Attorney, Agent, or Firm* — Greenblum & Bernstein, P.L.C.

(57) ABSTRACT

The data-accepting part accepts normal time information data and non-normal time information data, which are outputted from measurement equipment connected to the management apparatus, the data-identifying part identifies the normal time information data and the non-normal time information data based on the difference in the transmission path of the data, or based on identification information given to the data, and the data-output part outputs the above-mentioned normal time information data and the non-normal time information data, such that an operator identifies the information data.

14 Claims, 5 Drawing Sheets

MANAGEMENT APPARATUS FOR MEASUREMENT EQUIPMENT

FIELD OF THE INVENTION

The present invention relates to an apparatus for managing measurement equipment.

BACKGROUND OF THE INVENTION

When, for example, manufacturers, sales companies and the like of various measurement equipments such as blood cell counting device, concentration measuring device and the like (hereinafter such supplying side is to be also referred to as supplier) deliver measurement equipments to various medical institutions (hereinafter to be also referred to as user), it is desirable to not only make delivery but also remotely monitor various kinds of information (operational information) relating to the state of use, measurement sensitivity and the like of the measurement equipments even after delivery and provide users with prompt service and support regarding maintenance, accuracy management and the like. Such services and support are unique to measurement equipment requiring daily continuous maintenance.

Therefore, many suppliers connect measurement equipment delivered to users to a management apparatus (usually a server computer) on the supplier side via a communication terminal and a communication line attached to the measurement equipment to enable data communication, remotely monitor information data relating to the state of the measurement equipment by the management apparatus, and provide various services and support relating to the measurement equipment based on the monitoring results (e.g., patent document 1 and the like).

Figure 5A:
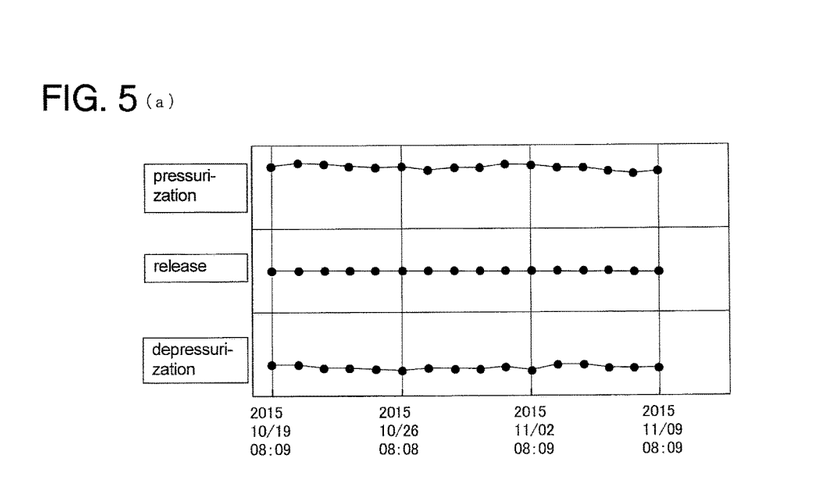
FIGS. 5(a) and 5(b) are diagrams illustrating problems of the conventional management apparatus that the present inventors have noted, and is a graph showing one embodiment of a mode of display of the information data of the measurement equipment outputted from the management apparatus to the display device. As one embodiment of the information data, similar to FIG. 3(a), measured data of the pressures at the time of pressurization, release of atmospheric pressure, and depressurization of a pump in the measurement equipment are shown.

In a more detailed example, a user who uses measurement equipment operates the measurement equipment for, for example, the analysis of specimen. The measurement equipment automatically measures the state of each part of the equipment itself through a sensor and the like set inside. The measurement equipment stores the results thereof as information data at the time of normal operation by the user (i.e., information data at a normal time, not a special situation) in the storage (memory) device in the measurement equipment. Further, the measurement equipment transmits the information data at the normal time to the management apparatus via a communication path (e.g., communication device, communication line and the like) at a normal time. The management apparatus accumulates the information data at the normal time received from the measurement equipment in the storage device, and displays same on the screen of the display device as, for example, a graph over time as shown in FIG. 5(a) and the like. The person in charge of monitor on the supplier side monitors the graph and the like and promptly and appropriately provides various services and support relating to the measurement equipment to the user according to the state of the measurement equipment indicated in the graph.

[patent document 1] JP-A-2008-249590

When an unexpected problem (e.g., operational problem and the like) occurs in the measurement equipment, the measurement equipment is brought to the supplier side for adjustment depending on the problem. The person who adjusts same on the supplier side adjusts and operates the measurement equipment while checking the state of each part of the equipment.

However, when the present inventor detailedly examined a case where the measurement equipment is adjusted and operated in a state other than the normal state, namely, non-normal time state, as mentioned above, it was found that the following problem may arise in conventional management apparatuses.

For example, the measurement equipment also stores the information data of each part of the apparatus, when operated in the non-normal state, in the storage device in the apparatus. The coordinator transmits the information data at such non-normal time to the management apparatus as a part of continuous record, and the management apparatus records the received information data at a non-normal time as data indicating the state of the measurement equipment. The problem is that the management apparatus does not recognize the transmitted information data as data at a non-normal time, handles it in the same manner as with the information data at a normal time, and outputs same to the display device and the like in the same way. When the management apparatus treats the information data at a normal time and the information data at a non-normal time without discrimination, the following confusion may occur in the service on the supplier side.

Figure 5B:
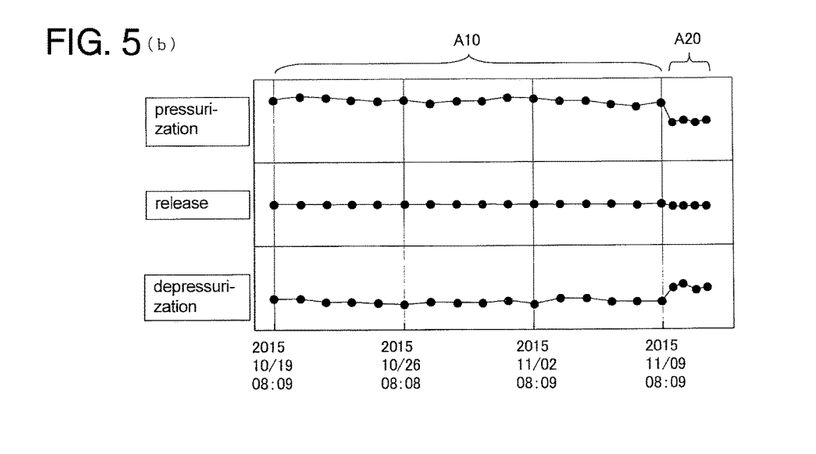

The management apparatus displays information data at a normal time, which is received from the measurement equipment before non-normal time (that is, at the time of normal operation on the user side), on the screen of the display device as a time-course graph (plots A10 in graph of FIG. 5(b). The graph indicates change in the measured data of respective pressures at pressurization, atmospheric pressure release, and depressurization in a pump in medical equipment, as one embodiment of the information data. However, the information data of non-normal time (adjustment time in this example) may sometimes be greatly different from plot A10 of the information data at a normal time before that, thus reflecting the change of parts and sensors, as shown as the last four plots A20 in the graph of FIG. 5(b). For example, when a person in charge of monitor on the supplier side sees the plot A10 at the normal time and the plot A20 at the non-normal time as shown in FIG. 5 (b) before knowing the information that the measurement equipment is adjusted, the person in charge of the monitor may recognize that the state of the measurement equipment is abnormal. This is the above-mentioned confusion of service on the supplier side.

In view of the aforementioned problem, an object of the present invention is to provide a management apparatus capable of informing an operator that the information data at a non-normal time obtained from the measurement equipment is that of a non-normal time when the information data is recorded in the management apparatus.

SUMMARY OF THE INVENTION

The main constitution of the present invention is as follows.

[1] A management apparatus for measurement equipment, the management apparatus comprising,
a data-accepting part, a data-identifying part, and a data-output part, wherein
the data-accepting part accepts information data at a normal time and information data at a non-normal time, which are outputted from a measurement equipment connected to the management apparatus,
the data-identifying part identifies the information data of the normal time and the information data of the non-normal time, which are accepted by the data-accepting part, based on the difference in the transmission path of the information data, or based on identification information given to one or both of the information data, and the data-output part outputs the above-mentioned information data of the normal time and the information data of the non-normal time, which are identified by the data-identifying part, such that the operator of the management apparatus identifies the information data.

[2] The management apparatus according to [1], wherein the data-identifying part carries out one or both of the processing of the following (i) and (ii) on the normal time information data and the non-normal time information data, which are identified based on the difference between the transmission paths of the information data, (i) a processing to give identification information to at least one of the normal time information data and the non-normal time information data for distinguishing one of them from the other, (ii) a processing to store the normal time information data and the non-normal time information data in a storage part as the data sets different from each other.

[3] The management apparatus according to [1] or [2], wherein the data-output part displays the normal time information data and the non-normal time information data on a displaying part in display forms different from each other, such that an operator of the management apparatus identifies the information data.

BRIEF DESCRIPTION OF THE DRAWINGS

FIGS. 3(a)-3(c) are graphs showing an embodiment of a mode of display of the information data of each of the normal time and the non-normal time identifiably outputted from the management apparatus to the display part in the Examples of the present invention. FIG. 3(a) shows the whole graph, and shows, as one embodiment of the information data, measured data of the pressures at the time of pressurization, release of atmospheric pressure, and depressurization of a pump in the measurement equipment. FIGS. 3(b) and 3(c) show a part of the plot of each of the normal time information data and the non-normal time in an enlarged manner.

DETAILED DESCRIPTION OF THE INVENTION

The management apparatus of the present invention accepts the normal time information data and the non-normal time information data, identifies them, and outputs the information data on a displaying part, so that an operator of the management apparatus can identify the information data. As a result, for example, even when the measurement equipment is suddenly adjusted and the information data at that time (non-normal time) is recorded in the management apparatus, the person who views the record can correctly recognize whether the information data is at a normal time or a non-normal time through the form shown on the display of the information data.

Figure 1:
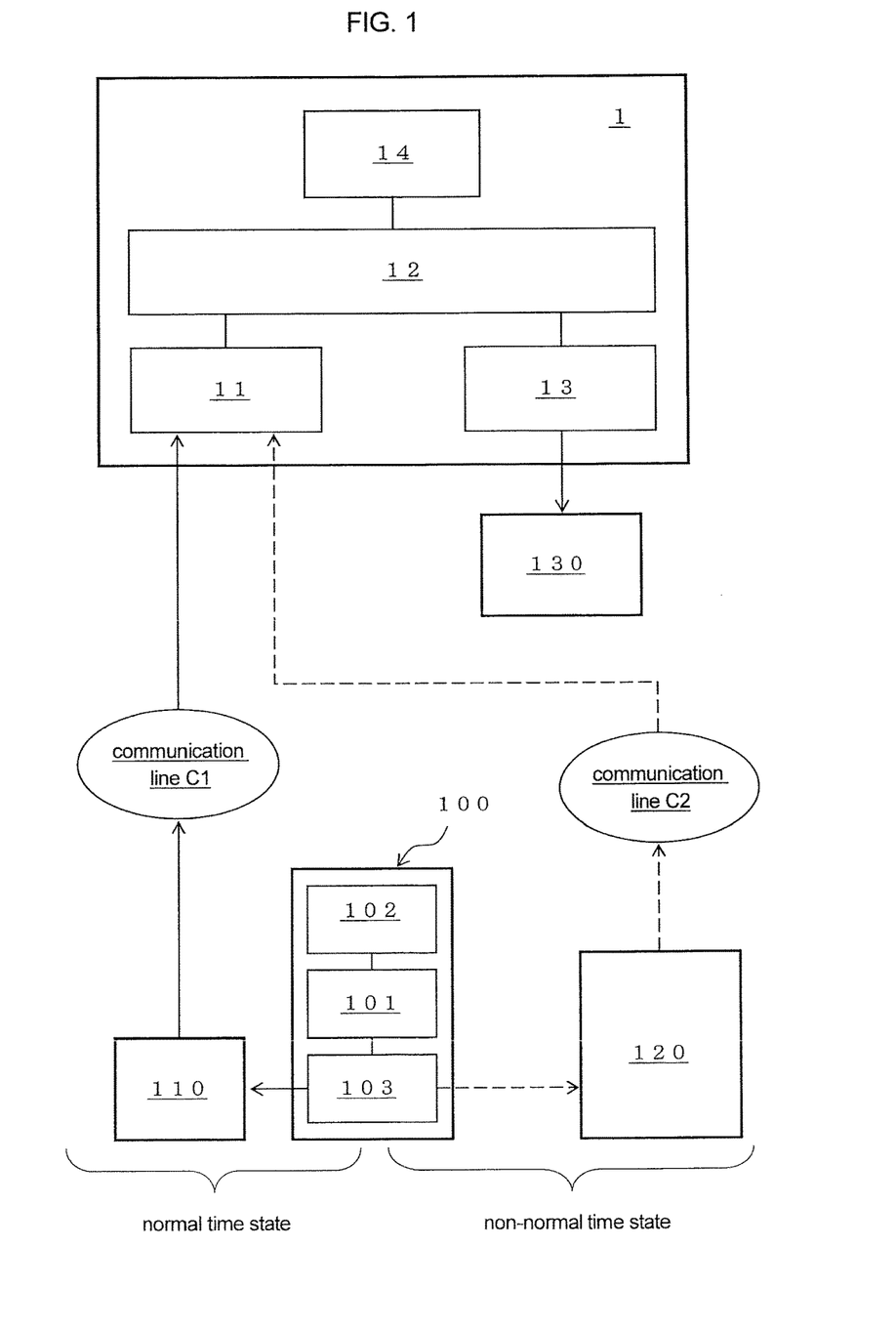
FIG. 1 is a block diagram showing the constitution of the management apparatus in the Examples of the present invention. In this drawing, while measurement equipment and a communication device are drawn separately for explanation, the communication device may be a communication part built in the measurement equipment. The thin line and the broken line showing the transmission path shows a path in which the information data are transmitted.

The constitution of the management apparatus of the present invention is explained in detail in the following by referring to Examples. In the following explanation, data-communicatable connection of the measurement equipment to the management apparatus is also simply referred to as connection of the measurement equipment to the management apparatus. FIG. 1 is a block diagram showing the constitution of the management apparatus in one examples of the present invention. FIG. 1 shows one measurement equipment 100 connected to a management apparatus 1 for explanation. A plurality of measurement equipment can be connected to the management apparatus 1, and the number of connections and the number of users are not particularly limited. The management apparatus 1 can remotely monitor the state of each measurement equipment of many connected users, acquire accuracy management information, operational information, maintenance information and the like of each measurement equipment, and record them continuously. The supplier side can promptly provide comprehensive maintenance service for measurement equipment of each user based on such information and records.

As shown in the example of FIG. 1, the management apparatus 1 is an apparatus for managing a measurement equipment 100, and is configured to comprise at least a data-accepting part 11, a data-identifying part 12, and a data-output part 13. In a preferable embodiment, the management apparatus 1 may have a storage part 14 on the inside or outside. The data-identifying part 12 may be a control part that controls data exchange between each part (data-accepting part, data-output part, storage part and the like) of the management apparatus 1, and may be a data-processing part. In the measurement equipment 100 connected to the management apparatus 1, a communication device 110 intervening the connection with the management apparatus 1 is attached to the inside or the outside of the measurement equipment, and the measurement equipment 100 delivered to the user can transmit the normal time information data to the management apparatus 1 through the communication device 110 and a communication line C1.

The normal time information data is, for example, information data indicating the state of each part of the measurement equipment which the measurement equipment internally records in the normal operation (e.g., measurement of specimens on the user side, operation for calibration using standard specimen, idle operation to measure blank value without specimen when the equipment is activated and the like) of the measurement equipment.

In contrast, the non-normal time information data includes, for example, [information data outputted from the measuring instrument when the operator on the user side or the supplier side adjusts the measurement equipment and the like, in a state in which the measurement equipment recognizes that it is a non-normal time by a switch for a non-normal time provided in the measurement equipment or communication from an external device and the like], [information data extracted from the measurement equipment through a transmission path different from the transmission path of the information data during the above-mentioned normal operation], and the like.

Therefore, the state of the non-normal time can be a special state, for example, a state in which an operator has logged in to the measurement equipment with administrator authority, a state in which it is inputted to the measurement equipment that it is a non-normal time through the above-mentioned switch for the non-normal time, a state in which the measurement equipment is informed from the outside that it is a non-normal time, a state in which information data is transmitted through a pathway for a non-normal time (copy of information data to USB memory and the like) and the like, and other states can be said to be normal time states. The distinction between the normal time and non-normal time can be determined as appropriate.

In the following explanation, the normal time information data is also referred to as the "normal data", and the non-normal time information data is also referred to as the "non-normal data".

The data-accepting part 11 is configured to accept the normal time information data and the non-normal time information data, which are outputted from the measurement equipment 100 connected to the management apparatus 1. In the example of FIG. 1, when the measurement equipment 100 is in the normal state, similarly to the conventional technique, normal data is transmitted to the data-accepting part 11 through the communication device 110 and a communication line C1. On the other hand, when the measurement equipment 100 is in the non-normal state, information data is transmitted to the data-accepting part 11 through a communicable external device (a computer for adjustment, and the like) 120 used for adjustment and the like, a communication line C2 and the like. In the example of FIG. 1, in a non-normal time, a USB memory is connected to the USB port of the measurement equipment 100, the information data is transferred to the USB memory, then the USB memory is connected to a USB port of the external device 120, and the information data is transmitted to the data-accepting part 11 through the external device 120 and the communication line C2. However, as mentioned below, the transmission path of the non-normal data is not particularly limited.

The procedure for transmitting information data from the measurement equipment to the management apparatus may be a procedure in which the management apparatus accepts transmission in response to a request from the measurement equipment, or conversely, a procedure in which the measurement equipment transmits in response to a request from the management apparatus. These transmissions may be periodically performed automatically, manually, or both automatically and manually.

The data-identifying part 12 identifies the aforementioned the normal time information data and the non-normal time information data accepted by the data-accepting part 11. The data-identifying part 12 utilizes difference in the transmission path of the information data or identification information given to one or both of the information data as a basis for identifying whether the accepted information data is normal data or non-ordinary data. Both of the difference in the transmission path of the information data and the identification information given to one or both of the aforementioned information data may be used as a basis for identification. In a preferable embodiment, normal data and non-normal data are identifiably stored in a storage part 14. The basis for identifying the information data and the mode for storing identifiably is described in detail below.

The data-output part 13 outputs the normal data and non-normal data identified by the data-identifying part 12 to a displaying part 130 such that an operator of the management apparatus identifies them. The displaying part 130 may be any as long as it is a device capable of displaying information data to the operator, such as a display device attached to the management apparatus, a display device of an outside computer, a printer and the like. The displaying part 130 and the external device 120 may be a single, same device. The embodiment of the displaying part 130 and display are mentioned below.

By the above-mentioned configuration, for example, even when the measurement equipment 100 is suddenly adjusted and the information data at that time (non-normal time) is recorded in the management apparatus 1, the person who views the record can correctly recognize whether the information data is at a normal time or a non-normal time through the form shown on the display of the information data.

Each part constituting the management apparatus (e.g., data-accepting part 11, data-identifying part 12, data-output part 13) may be constituted by a combination of electronic circuit, electric circuit, separate processing unit, communication equipment and the like. In a preferable embodiment, each of these parts are constituted by a computer and using a program executed by the computer as shown in FIG. 2.

A preferable embodiment and an effect thereof are explained in the following by referring to an Example when the management apparatus is constituted by a computer. The constitution of each part described below can be performed instead of a computer by partly or entirely combining an electronic circuit, an electric circuit, an independent processing device, a communication device and the like.

Figure 2:
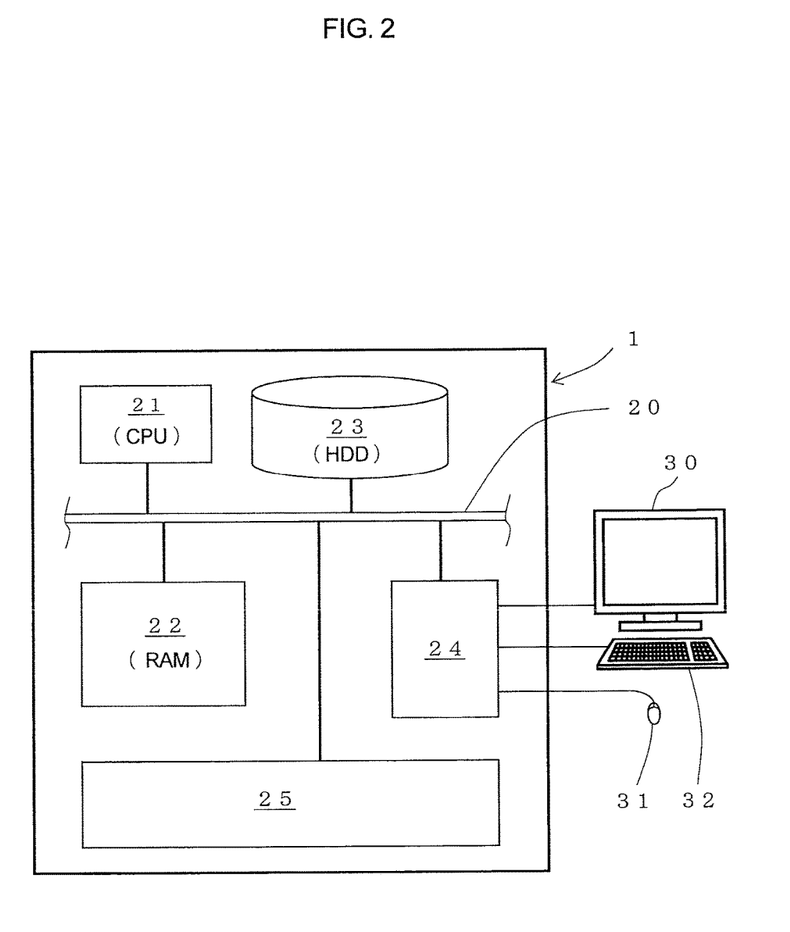
FIG. 2 is a block diagram showing an embodiment in which the management apparatus is composed by a computer in the Examples of the present invention.

FIG. 2 is a block diagram showing a preferable example of the management apparatus, and shows an example wherein the management apparatus is constituted by a computer. In the example of FIG. 2, the management apparatus 1 may be a server computer for remotely managing measurement equipment delivered to users for maintenance services. The basic architecture itself of the management apparatus 1 as a computer shown in FIG. 2 may be the same as the conventionally known computer. As shown in FIG. 2, a computer as the management apparatus 1 has a constitution wherein a central processing unit (CPU) 21 and a main memory (RAM in the example of FIG. 2) 22 are connected by a data bus 20, preferably a hard disk drive (HDD) 23 is connected and gives CPU 21 a storage area with large capacity. The hard disc drive 23 may be appropriately replaced by other storage device such as solid-state drive and the like. In addition, it may be connected to an external storage device or external computer so that large amounts of data continuously obtained from many measurement equipments can be stored.

In the example of FIG. 2, display device 30, mouse 31 and keyboard 32 are connected to a data bus 20 via an interface 24, as a displaying part and an input part attached to the management apparatus itself which is a computer. These displaying part and input part can also be used, for example, by an administrator of the management apparatus to change or update the contents and the like of the program executed by the management apparatus as necessary, and can also be used for the analysis of the records accumulated in the management apparatus by an operator of the management apparatus.

When the management apparatus is a computer, the data-accepting part 11 and data-output part 13 shown in FIG. 1 are the parts where the computer works according to the program executed in the computer. In other words, the program is constituted to cause a computer as the management apparatus to function as data-accepting part 11, data-identifying part 12, and data-output part 13. Each of the above-mentioned functions (operation contents) achieved by executing the program includes not only processing performed by CPU 21 and main memory 22, but also the functions achieved by using each hardware constituting the management apparatus and external hardware, under the instruction by the program. Furthermore, by the control of the program, the function of each part may be executed in an external device connected to the management apparatus, and function of each part may be executed by the cooperation of the management apparatus and the external device. Also, the management apparatus may be configured as a form of a virtual server.

In the example of FIG. 2, the data-accepting part 11 and data-output part 13 of FIG. 1 are parts that perform data communication with an external device, store data in a storage device, and take out data from a storage device. These data-accepting part 11 and data-output part 13 can be constituted using at least CPU 21, main memory 22 and interface 25 (further using hard disc drive 23 and external storage device as necessary), under execution of the computer program. Similarly, the data-identifying part 12 can also be constituted using at least CPU 21 and main memory 22 under execution of the computer program.

Here, to explain an embodiment wherein data-identifying part 12 identifies normal data and non-normal data, examples of a measurement equipment connected to the management apparatus, and a transmission path of each of the normal data and the non-normal data are shown below.

While the measurement equipment 100 to be connected to the management apparatus is not particularly limited, equipment preferable for performing service by remote management such as continuous monitoring and the like makes the usefulness of the present invention remarkable. Examples of such measurement equipment include equipment that can measure and analyze items relating to various tests (hematological examination, biochemical examination, immunological examination, genetic examination) using a specimen (blood, urine, feces, cell and the like) as a test target. For example, blood cell counting device, blood analysis device, concentration measuring device, immunity measuring device, device for genetic analysis and the like can be mentioned.

The measurement equipment 100 to be connected to the management apparatus preferably has an output port (wiring output terminal and/or wireless transmitting and receiving part and the like), such that an operator and the like output information data for performing maintenance service to an external device. Many measurement equipments in recent years have a control part 101 (usually a central processing unit of a computer) and a storage part 102, and has an interface 103 for data communication with the outside as an output port, even when they are compact instruments such as desktop type and palm size (palmtop type) and the like, as shown in FIG. 1, and can output the information data to the external device. In the communication with the external device such as the management apparatus and the like, the measurement equipment holds identification information (measurement equipment ID) for identifying other measurement equipment, in the storage part 102 and the like. The management apparatus 1 identifies each measurement equipment based on the measurement equipment ID of each measurement equipment, collects and accumulates information data for each measurement equipment. As for the technology of data communication between each measurement equipment and the management apparatus, conventional technology can be referred to. The communication of the information data may be constituted such that it is started under the initiative of either the measurement equipment side or the management apparatus, for example, the measurement equipment periodically requests the management apparatus to start data communication, and the management apparatus starts data communication in response to the request and the like, or both sides request communication of information data to the other party and receive a response.

The information data (normal data and non-normal data) outputted from the measurement equipment are not particularly limited, and vary depending on the mechanism of the measurement equipment and test contents. Examples of the items of representative information data include pump pressure values (values at the time of pressurization, release of atmospheric pressure, and depressurization and the like) shown in FIGS. 3(a)-3(c), measured values (count value, measured raw data value) of standard sample measurement and blank measurement and specimen measurement, temperature value (temperature of temperature-adjusting part voltage), values of measurement part sensor and the like, values of required time (time before start-up and the like), operating/action history and information of set value and the like.

The information on the date (may include time) is preferably given to the normal data and non-normal data. Based on the date information, the data-output part can manage these information data in the order of the passage of date and output same to the displaying part.

In the example of FIG. 1, the communication device 110 attached to the measurement equipment 100 is drawn to be a communication device other than the measurement equipment 100 for easy understanding as a block diagram. However, it may be a communication device part built in the measurement equipment or a separate communication device data-communicatably connected to the measurement equipment.

A communication line (communication line used for transmitting normal data) C1 between communication device 110 and the management apparatus may be wired or wireless, or may be a combination thereof. Examples of the communication line include any available communication lines such as wired or wireless local area network (LAN), Internet, telephone line, mobile broadband (wireless broadband) and the like. These can be used alone or in combination with any combination of these. A local section such as a terminal part of a communication line and the like may contain a communication path conforming to an interface such as Bluetooth (registered trade mark), USB, RS-232C and the like. The communication line C1 is preferably a wireless communication line such as mobile broadband and the like to place measurement equipment without introducing wiring in the medical field, and to eliminate the trouble of wiring connection. In the example of FIG. 1, a transmission path having the communication unit 110 and the communication line C1 used at the above-mentioned normal time is the transmission path of the normal time.

On the other hand, in the state of a non-normal time, the non-normal data may be transmitted to the management apparatus through the above-mentioned transmission path of a normal time or a transmission path of a non-normal time, which is a transmission path other than the transmission path of a non-normal time.

First, transmission of the non-normal data to the management apparatus through the above-mentioned transmission path of a normal time is explained. For example, in the example of FIG. 1, when an engineer on the supplier side adjusts the measurement equipment 100 at the user's place or takes the measurement equipment 100 and the communication device 110 back to the supplier side and the like, the non-normal data can be transmitted to the management apparatus 1 in the same transmission path as the normal data (that is, through the communication device 110 and the communication line C1). When the non-normal data are transmitted through a transmission path at a normal time, it is preferable to give information for identification to the information data as in the following embodiments (a)-(c), such that a data-accepting part in the management apparatus recognizes non-normal data as non-normal data.

(a) Embodiment wherein measurement equipment gives identification information such as a flag and the like indicating that it is non-normal data to non-normal data, and does not give such identification information to normal data.

(b) Embodiment wherein measurement equipment gives identification information such as a flag and the like indicating that it is normal data to normal data, and does not give such identification information to mpm-normal data.

(c) Embodiment wherein measurement equipment gives identification information such as a flag and the like indicating that it is non-normal data to non-normal data, and also gives identification information such as a flag and the like indicating that it is normal data to normal data.

To preferably perform the embodiments of the aforementioned (a)-(c) for identification, for example, the measurement equipment is configured such that it can switch between a mode for outputting normal data (normal mode) and a mode for outputting non-normal data (non-normal mode). More specifically, an embodiment wherein a switch or a button is provided on the measurement equipment side (operation panel, backside, inside and the like) so that the normal mode and the non-normal mode can be switched, and an embodiment wherein the control part 101 of the measurement equipment switches between the normal mode and the non-normal mode on receipt of an command signal from the management apparatus or external controller can be mentioned. In the aforementioned embodiment (a), when the operator switches to the non-normal mode and acquires and transmits the information data, the control part 101 of the measurement equipment 100 gives identification information such as a flag and the like indicating non-normal data to the information data, and outputs same as non-normal data from the interface 103 to the communication device 110. In the aforementioned embodiment (b), when the operator switches to the non-normal mode and acquires and transmits the information data, the control part 101 of the measurement equipment 100 does not give, to the non-normal data, the identification information it gave to the normal data. The lack of this identification information serves as a marker for non-normal data. In the aforementioned embodiment (c), when the operator switches to the non-normal mode and acquires and transmits the information data, the control part 101 of the measurement equipment 100 changes the identification information gave to the normal data to identification information indicating non-normal data, gives same to the non-normal data and outputs same as the non-normal data. By constituting the measurement equipment 100 such that these embodiments can be performed, whether the information data outputted from the measurement equipment is normal data or non-normal data can be identified, and the data-identifying part 12 of the management apparatus can recognize that the information data is non-normal data.

There is a case where some kind of trouble occurs in the communication state when the measurement equipment transmits normal data to the management apparatus, and the normal data cannot be transmitted. To deal with such case, the measurement equipment may be constituted to accumulate normal data that could not be transmitted due to the trouble of the communication in the storage part, and transmit the non-transmitted normal data accumulated in the storage part to the management apparatus together with the latest normal data (or only the non-transmitted normal data) after the trouble of the communication is resolved. In such case, the data-accepting part 11 of the management apparatus may be constituted to accept the aforementioned non-transmitted normal data, which are transmitted from the measuring equipment, and the data-identifying part 12 may be constituted to identify the normal data and store same in the storage part.

As the aforementioned identification information, information of 1 bit or more can be used. The identification information may be given to each piece of data or may be given to a file name and the like indicating the entire data set to be transmitted. Prior to the transmission of the data, identification information for transmitting normal data or non-normal data may be transmitted from the measurement equipment to the data-accepting part of the management apparatus.

In the state of a non-normal time, as shown in FIG. 1, the information data may be transmitted to the management apparatus through a transmission path (e.g., movement of information data using a storage medium such as the above-described USB memory and the like, a path through a communicatable external device 120 and communication line C2 and the like) different from the above-described normal time transmission path. In this case, a port for outputting information data from the measurement equipment 100 to the external device 120 may be an input/output interface formed on the measurement equipment, such as a port for outputting information data to the above-mentioned communication device 110 (input-output interface), Bluetooth (registered trade mark), USB (Universal Serial Bus), RS-232C and the like. Among others, USB is a preferable input-output interface in that it is provided in many measurement equipments in recent years, and the measurement equipment 100 and the external device 120 may be connected by a USB cable, or information data may be transferred via a storage device having a USB terminal such as the above-mentioned USB memory and the like. In such case, the control part 101 is preferably constituted such that when the operator switches the measurement equipment to a non-normal mode by a switch or button, the data are outputted from the USB port to USB memory.

The communication line C2 between the external device 120 and the management apparatus may be wired or wireless, and various communication lines such as a line including a wireless line such as a wireless LAN and Wi-Fi (registered trade mark) and the like and the Internet, a mobile broadband line and the like can be preferably used. The communication line C2 may be a line similar to communication line C1.

When non-normal data is transmitted to the management apparatus through a transmission path different from the transmission path at a normal time, non-normal data may be given identification information showing that it is non-normal data as mentioned above. However, data-identifying part 12 of the management apparatus 1 may be constituted such that it can recognize and identify the non-normal data as non-normal data based on the difference in the transmission path of the information data (difference in the data transmission source) even without such identification information. For example, in FIG. 1, when the information data at the time of adjustment is taken out from the USB interface provided in the measurement equipment 100 to an external device (computer for adjustment) 120, and the information data is transmitted to the management apparatus, the data-identifying part 12 recognizes the information data as non-normal data, namely, identifies normal data and non-normal data, based on the difference in the transmission path of the information data (i.e., based on communication line C2 used not being communication line C1 of a normal time, or based on transmission source (external device 120) of the information data not being transmission source of a normal time (communication device 110)), and can process these data so that they can be handled to be identified as data-output part and the like.

When information data is outputted through an input-output interface other than input-output interface (USB and the like) used at a normal time, or when information data is outputted to the external device 120 other than the communication device 110 used at a normal time, the measurement equipment 110 may give identification information such as a flag and the like indicating that the information data is non-normal data, based on the difference in the transmission path of the information data (i.e., based on the input-output interface used not being an input-output interface of a normal time, or based on transmission source (external device 120) of the information data not being transmission source of a normal time (communication device 110)), and may output as non-normal data. In addition, the external device 120 may give identification information, to the information data, such as a flag and the like indicating that the information data is non-ordinary data of the time point when the external device 120 takes out the information data from the aforementioned interface (USB and the like) of a non-normal time.

The aforementioned movement of information data through the interface of a non-normal time may be movement through wired or wireless communication, movement via a storage medium such as USB memory.

As described above, the normal data and non-normal data can be each identified based on the difference in the transmission path (difference in the communication line, difference in the transmission source), or based on the identification information given to one or both of these data. Therefore, the data-identifying part of the management apparatus can also identify the normal data and non-normal data based on the aforementioned difference in the transmission path or the identification information given to one or both of these data and process them as mutually identifiable data.

The data-identifying part 12 may be constituted to perform one or both processing of the following (i) and (ii) on the normal time information data and the non-normal time information data identified based on the difference in the transmission path of the information data.

(i) Processing of at least one of the normal time information data and the non-normal time information data to give identification information for distinguishing same from the other. When the identification information is already given to the accepted normal data and non-normal data, the data-identifying part 12 may directly use the identification information for identification, or give other identification information according to the processing in the management apparatus. When identification information is given, similar to the above-mentioned embodiments (a)-(c), (a1) embodiment wherein identification information for non-normal is given only to non-normal data, (b1) embodiment wherein identification information for normal is given only to normal data, or (c1) embodiment wherein identification information for normal is given to normal data and identification information for non-normal is also given to non-normal data may be employed. The identification information is given to the data in the same manner as above.

(ii) Processing of storing the normal time information data and the non-normal time information data as the data sets different from each other in the storage part. For example, the data-identifying part 12 may store the non-normal data in the non-normal data file of the storage part 14 or other storage part (not shown) such that the normal data and the non-normal data are identifiable.

Either one or both of the above processes (i) and (ii) may be performed. Either one or both of identification of information data based on the difference in the transmission path and identification of information data based on the identification information given to one or both of the information data may be performed. The processing of the above-mentioned (ii) is a preferable processing since identification information does not need to be added to the information data.

The data-output part 13 outputs the normal data and the non-normal data which are regarded as mutually identifiable data as described above to a displaying part for display. At this time, the data-output part 13 displays the normal data and the non-normal data in mutually different displaying forms such that the operator of the management apparatus identifies them. A display-image creating part may be further provided for creating an image for displaying the normal data and the non-normal data in mutually different display forms. The operator is not particularly limited and may be, for example, a person who accesses the management apparatus through an input/output device attached to the management apparatus or through an external device, such as monitor personnel on the supplier side and the like.

While the displaying forms for displaying the normal data and non-normal data, which are different from each other, are not particularly limited, the following embodiments can be mentioned as examples thereof.

Figure 3A:
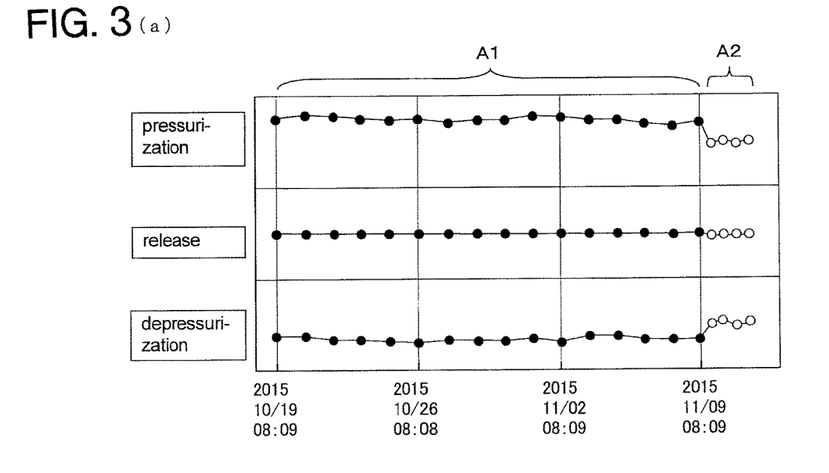
Figure 3B:
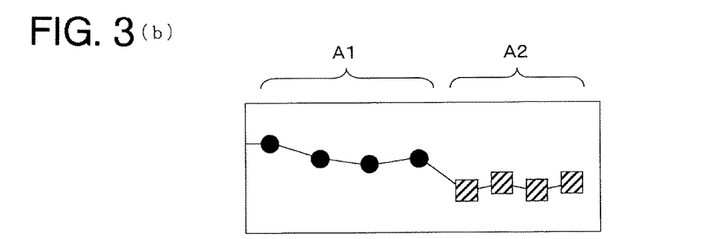

An embodiment wherein the colors and patterns of the plot symbols are different between normal data and non-normal data as shown in the graphs of FIG. 3(*a*), (*b*). In the example of FIG. 3(*a*), plot A1 of normal data is a black circle and plot A2 of non-normal data is a white circle. A line indicating the outer shape of the plot may be added as appropriate. In the example of FIG. 3(*b*), plot A1 of normal data is a black color, and plot A2 of non-normal data has a hatching pattern. Combinations with large differences in shading such as black and white, red and white and the like, and combinations of patterns are preferable since the operator can recognize the difference, whether the displaying part is a color display device or a black-and-white display device. For a color display device, it is preferable to use a combination of colors and patterns that allow the operator to more strongly recognize the difference. Not only hatching but also various patterns that make the difference between plots become clear, such as dot and the like, can be used.

An embodiment wherein the shape of plot symbols is different from each other as shown in the graph of FIG. 3(b): In the example of FIG. 3(b), the symbol of plot A1 of normal data is a circular shape and plot A2 of non-normal data is a rectangle. The shape of the symbol is not limited, and various shapes such as double circle, triangle, star-shape and the like can be used. It is preferable to combine shapes that make the difference between plots more clear to the operator.

Figure 3C:
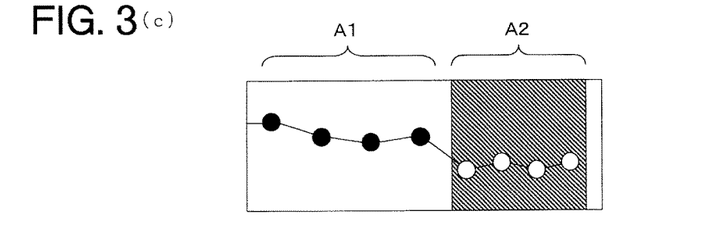

An embodiment wherein the colors and patterns of zones in the plotted graphs are different from each other as shown in FIG. 3(c): In the example of FIG. 3(c), hatching is applied only to the zone in which plot A2 of non-normal data is located. The color and pattern of the zone are not particularly limited, and a combination of colors and patterns of the zone that enables the operator to more strongly recognize the difference is preferably used. The color of the plot may be selected according to the color of the zone so that the operator can easily recognize the plot.

Not only the above-mentioned embodiments, but also any display form can be adopted, in which an operator can identify normal data and non-normal data, such as an embodiment wherein normal data and non-normal data are displayed in different graphs and tables, an embodiment wherein lines in the graph are different (combination of thick line and broken line and the like), an embodiment wherein the color of lines in the graph is different, an embodiment wherein annotation showing normal data and/or non-normal data is displayed and the like.

Normal data and non-normal data may be displayed at the same time or only one of them may be displayed. The normal data and the non-normal data may be displayed in different windows on the display screen or may be displayed on different display devices.

While the display forms described above may be performed alone, or two or more of the above display modes may be appropriately combined to aid the operator's identification. For example, as shown in FIG. 3(b), an embodiment wherein the shape and color of the plot differ from each other between plot A1 of normal data and plot A2 of non-normal data, an embodiment wherein the color of zone in the graph is different from each other and the like can be mentioned.

For example, the main memory 22, the hard disk drive 23 and the like in FIG. 2 may be formed, and an outside storage device may be used as necessary in a storage part for storing normal time data and non-normal time data for each measuring equipment. In addition, a data processing part for identifiable processing of normal-time data and the non-normal-time data may be additionally provided. The data-accepting part, data-output part or data-processing part may be constituted to inform the operator of abnormality when normal time data indicates abnormality.

The displaying part 130 through which the data-output part 13 shows normal data and non-normal data to the operator may be a display device attached to the management apparatus itself, a display device attached to an external device (such as a terminal computer, portable information terminal and the like) capable of data communication with the management apparatus, a printer connected to the management apparatus or external device and the like.

The communication line in this case may be wiring, wireless, the same line as the communication lines C1, C2 described above, and a communication line capable of data-communicatably connecting the external device and the management apparatus can be used.

For example, a person in charge of monitoring on the supplier side can monitor the state of each measurement equipment outputted from the data-output part 13 by communicating with the management apparatus using the displaying part 130 and the communication line.

When the displaying part 130 is an external terminal computer and the information data of each measurement equipment accumulated in the management apparatus 1 is viewed through the display device of the terminal computer, a program for identifiably displaying the data on the display device may be a program to be executed on the terminal computer (program for accepting identifiable data and identifiably displaying the data for the operator), or an embodiment wherein a display program to be executed on the management apparatus (computer) is utilized by each terminal computer.

As the program on the management apparatus side, various conventionally known programming languages such as Java (registered trade mark) and the like, which are used for creating a website, can be used, and a descriptive language such as HTML may also be used.

Figure 4:
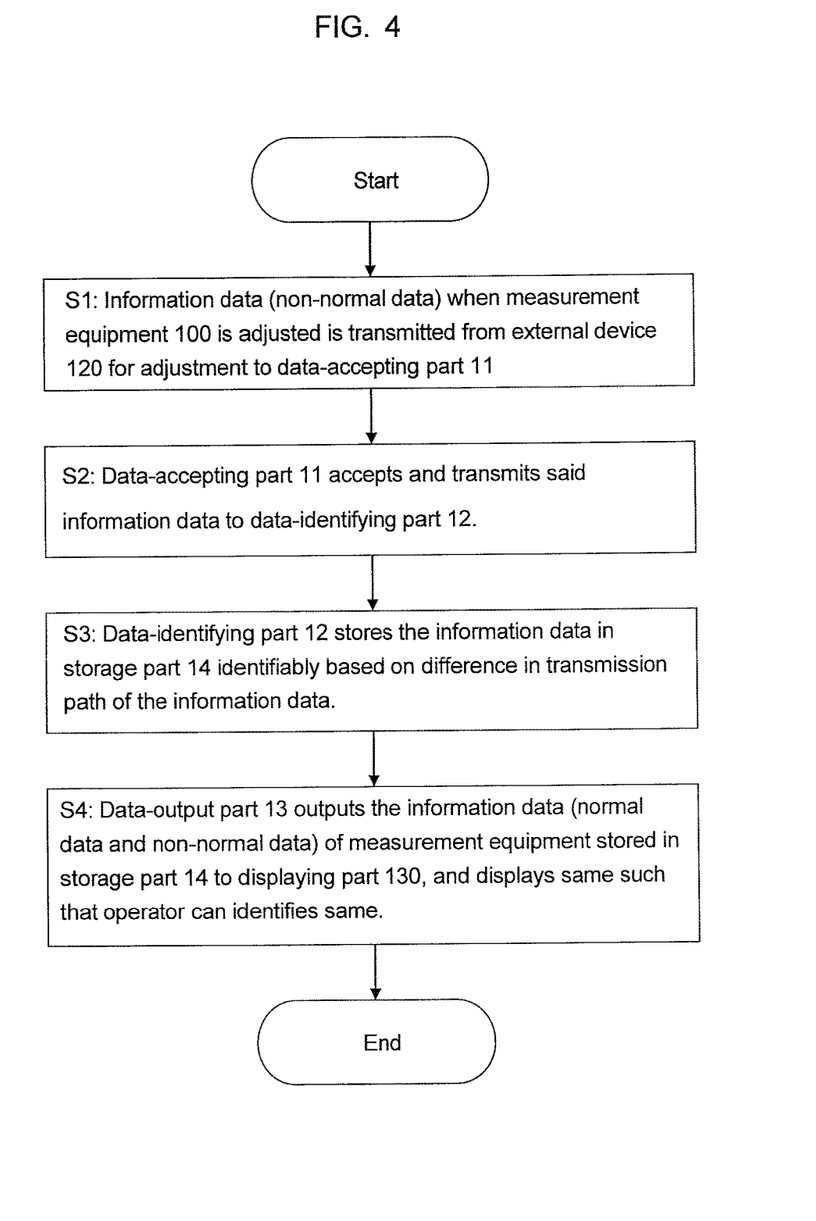
FIG. 4 is a flowchart, in the Examples of the present invention, illustrating a flow of processing by the management apparatus when information data outputted from the measurement equipment is recorded.

In the state of a non-normal time of the example shown in FIG. 1, one embodiment of processing step of each unit of the management apparatus when an operator adjusts measurement equipment 100, and transmits non-normal data to the management apparatus through an external device (computer for adjustment) 120 is explained along the flowchart shown in FIG. 4.

In step S1, the information data (non-normal data) when the measurement equipment 100 is adjusted is taken out from the measurement equipment 100, and transmitted from an external device (computer) 120 for adjustment to a data-accepting part 11. In this example, identification information for distinguishing normal data and non-normal data is not given.

In step S2, the data-accepting part 11 accepts the information data and transmits the information data to the data-identifying part 12.

In step S3, the data-identifying part 12 stores the information data in a non-normal data file in a storage part 14 based on the difference in the transmission path of the information data (based on external device 120 as transmission source in this example, but it may be based on the use of communication line C2).

In step S4, the data-output part 13 outputs, in response to the request of the operator, the information data (normal data and non-normal data) of the measurement equipment identifiably stored in the storage part 14 to an outside computer for monitoring, and displays same on a display device (display device attached to the computer) 130 so that the operator can identify same.

When the adjustment is completed, the measurement equipment is returned to the user, and connected as the original normal state to the management apparatus via a communication device, used by the user, and the normal data are transmitted to the management apparatus. At this time, the past information data accumulated in the measurement equipment may also be transmitted in addition to the latest normal data. When non-normal data at the time of adjustment is included in the past information data, the measurement equipment may unidentifiably transmit the non-normal data as a part of the normal data. When the management apparatus receives such information data, non-normal data already identifiably stored and unidentifiable data received as a part of the normal data overlap in the management apparatus. In such case, the data-identifying part 12 may hold both the unidentifiable non-normal data received later and previously stored identifiable non-normal data, or the unidentifiable non-normal data accepted later may overwrite the previous identifiable non-normal data, or eliminate the unidentifiable non-normal data accepted later by placing priority on the previous identifiable non-normal data. Even when the unidentifiable non-normal data accepted later is to be overwritten, the supplier side is not confused since the person in charge of monitoring already knows the facts of adjustment of measurement equipment and the like and the existence of non-normal data.

In the above-mentioned embodiments, the measurement equipment used in the medical field is cited as an example of the management target of the management apparatus. However, the measurement equipment to be the management target of the management apparatus may be measurement equipment (including measurement equipment and analysis device) in not only the medical field but also any industrial field. For example, in the field of environmental measurement, the quality of river water, air pollution and the like are continuously measured by measurement equipment. The management apparatus can perform such continuous measurement and can preferably manage measurement equipment that requires continuous management for that measurement.

In addition, the management apparatus may be a management apparatus for measurement equipment, comprising
    a data-accepting part, a data-identifying part, and a storage part,
    wherein
    the data-accepting part accepts the normal time information data and the non-normal time information data, which are outputted from measurement equipment connected to the management apparatus,
    the data-identifying part identifies the aforementioned normal time information data and the non-normal time information data accepted by the data-accepting part based on the difference in the transmission path of the information data, or
    identifies based on the identification information given to one or both of the aforementioned information data, and
    the storage part stores the aforementioned normal time information data and the non-normal time information data identified by the data-identifying part.

The constitution wherein the management apparatus of the present invention and measurement equipment are data-communicatably connected can also be said a management system for measurement equipment, which comprises the management apparatus and measurement equipment (further, an external device accessible to the management apparatus).

While the management apparatus is connected to the measurement equipment such that the operational information of the measurement equipment is remotely monitored, the connection aims at services and support for the user of the measurement equipment itself. Therefore, it is preferable to prevent unintentional transmission, from the measurement equipment to the management apparatus, of such information (e.g., information that can identify individual person such as specimen ID and the like) relating to the specimen handled by the measurement equipment on the user side.

From such aspect, in a preferred embodiment of the management apparatus (or a management system including the management apparatus and the measurement equipment), a communication-setting part capable of setting one or both of the management apparatus and the measurement equipment enabling or disabling communication of the specimen information in them is preferably provided. Particularly, it is more secure and preferable to provide a communication-setting part to both the measurement equipment and the management apparatus because, even when the measurement equipment is set to enable communication of specimen information, the specimen information is not received by the management apparatus unless the management apparatus is set to enable communication of specimen information. Furthermore, it is a more preferable embodiment from the aspect of security to provide a constitution of the communication-setting part in the management apparatus, which prevents any one other than a person having specific authority on the supplier side from changing the setting of the communication-setting part to allow communication.

When, for example, non-normal data of measurement equipment are recorded in the management apparatus according to the present invention, an operator who viewed the records can correctly recognize that the non-normal data is the data of a non-normal time. Therefore, a misunderstanding of occurrence of abnormality in the measurement equipment and confusion in the service on the supplier side can be suppressed.

This application is based on a patent application No. 2016-010190 filed in Japan (filing date: Jan. 21, 2016), the contents of which are incorporated in full herein.

The invention claimed is:

1. A management apparatus for measurement equipment connected to the management apparatus, the management apparatus comprising:
    a processor that
        accepts measurement data representing values of a parameter measured by the measurement equipment at a first time during which the measurement equipment is in a predetermined state in response to i) an operation of a switch of the measurement equipment, ii) logging into the measurement equipment, or iii) receipt of a command signal from an external device,
        accepts measurement data representing values of the parameter measured by the measurement equipment at a second time during which the measurement equipment is in a state other than the predetermined state,
        identifies the accepted measurement data measured at the second time and the accepted measurement data measured at the first time, based on a difference in a transmission path of the measurement data measured at the second time and a transmission path of the measurement data measured at the first time, or based on identification information given to one or both of the measurement data measured at the second time and the measurement data measured at the first time,
        outputs the identified measurement data measured at the second time and the identified measurement data measured at the first time in mutually different display forms that permit an operator of the management apparatus to visually distinguish the measurement data measured at the second time from the measurement data measured at the first time when at least one of the measurement data measured at the second time and the measurement data measured at the first time is displayed; and
    a display that displays values of the parameter measured by the measurement equipment of at least one of
        the outputted measurement data measured by the measurement equipment at the second time, and
        the outputted measurement data measured by the measurement equipment at the first time, wherein a display form of the values of the parameter of the outputted measurement data measured by the measurement equipment at the second time and displayed by the display is visually different from the display form of the values of the parameter of the outputted measurement data measured by the measurement equipment at the first time and displayed by the display.

2. The management apparatus according to claim 1, wherein the processor carries out one or both of first processing and second processing on the measurement data of the second time and the measurement data of the first time, which are identified based on the difference between the transmission paths of the measurement data, wherein first processing provides identification information to at least one of the measurement data of the second time and the measurement data of the first time for visually distinguishing one from the other when displayed on the display, and wherein the second processing stores the measurement data of the second time and the measurement data of the first time in a memory as data sets that are different from each other.

3. The management apparatus according to claim 1, wherein the processor controls the display to display the measurement data of the second time and the measurement data of the first time in plots of mutually different colors and shapes.

4. The management apparatus according to claim 1, wherein the processor controls the display to display the measurement data of the second time and the measurement data of the first time in zones of a graph in mutually different colors.

5. The management apparatus according to claim 1, wherein the processor controls the display to display the measurement data of the second time and the measurement data of the first time in at least one of mutually different graphs and/or tables.

6. The management apparatus according to claim 1, wherein the processor controls the display to display the measurement data of the second time and the measurement data of the first time as different lines in a graph.

7. The management apparatus according to claim 1, wherein the processor controls the display to display the measurement data of the second time and the measurement data of the first time as different colored lines in a graph.

8. The management apparatus according to claim 1, wherein the processor controls the display to display an annotation to visually distinguish the measurement data of the second time and the measurement data of the first time.

9. The management apparatus according to claim 1, wherein the processor controls the display to display the measurement data of the second time and the measurement data of the first time at the same time.

10. The management apparatus according to claim 1, wherein the processor controls the display to display only one of the measurement data of the second time and the measurement data of the first time.

11. The management apparatus according to claim 1, wherein the processor controls the display to display the measurement data of the second time and the measurement data of the first time in different windows on a display screen of the display.

12. The management apparatus according to claim 1, wherein the processor controls the display to display the measurement data of the second time and the measurement data of the first time on different display devices.

13. A management method for a management apparatus for measurement equipment connected to the management apparatus, the management method comprising:

accepting, with a processor, measurement data representing values of a parameter measured by the measurement equipment at a first time during which the measurement equipment is in a predetermined state in response to i) the operation of a switch of the measurement equipment, ii) logging into the measurement equipment, or iii) receipt of a command signal from an external device;

accepting, with the processor, measurement data representing values of the parameter measured by the measurement equipment at a second time during which the measurement equipment is in a state other than the predetermined state;

identifying, with the processor, the accepted measurement data measured at the second time and the accepted measurement data measured at the first time, based on a difference in a transmission path of the measurement data measured at the second time and a transmission path of the measurement data measured at the first time, or based on identification information given to one or both of the measurement data measured at the second time and the measurement data measured at the first time;

outputting, with the processor, the identified measurement data measured at the second time and the identified measurement data measured at the first time in mutually different display forms that permit an operator of the management apparatus to visually distinguish the measurement data measured at the second time from the measurement data measured at the first time when at least one of the measurement data measured at the second time and the measurement data measured at the first time is displayed; and displaying, with a display, values of the parameter measured by the measurement equipment of at least one of the outputted measurement data measured by the measurement equipment at the second time and the outputted measurement data measured by the measurement equipment at the first time, wherein a display form of the values of the parameter of the outputted measurement data measured by the measurement equipment at the second time and displayed by the display is visually different from the display form of the values of the parameter of the outputted measurement data measured by the measurement equipment at the first time and displayed by the display.

14. A non-transitory computer-readable storage medium storing a program for instructing a computer to perform a management method for a management apparatus for measurement equipment connected to the management apparatus, the management method comprising:

accepting, with a processor, measurement data representing values of a parameter measured by the measurement equipment at a first time during which the measurement equipment is in a predetermined state in response to i) the operation of a switch of the measurement equipment, ii) logging into the measurement equipment, or iii) receipt of a command signal from an external device;

accepting, with the processor, measurement data representing values of the parameter measured by the measurement equipment at a second time during which the measurement equipment is in a state other than the predetermined state;

identifying, with the processor, the accepted measurement data measured at the second time and the accepted measurement data measured at the first time, based on a difference in a transmission path of the measurement data measured at the second time and a transmission path of the measurement data measured at the first time, or based on identification information given to one or both of the measurement data measured at the second time and the measurement data measured at the first time;

outputting, with the processor, the identified measurement data measured at the second time and the identified measurement data measured at the first time in mutually different display forms that permit an operator of the management apparatus to visually distinguish the measurement data measured at the second time from the measurement data measured at the first time when at least one of the measurement data measured at the second time and the measurement data measured at the first time is displayed; and displaying, with a display, values of the parameter measured by the measurement equipment of at least one of the outputted measurement data measured by the measurement equipment at the second time, and the outputted measurement data measured by the measurement equipment at the first time, wherein a display form of the values of the parameter of the outputted measurement data measured by the measurement equipment at the second time and displayed by the display is visually different from the display form of the values of the parameter of the outputted measurement data measured by the measurement equipment at the first time and displayed by the display.

* * * * *